(12) United States Patent
Smith

(10) Patent No.: US 8,409,086 B2
(45) Date of Patent: Apr. 2, 2013

(54) SURGICAL PORTAL WITH ROTATING SEAL

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 160 days.

(21) Appl. No.: 12/961,531

(22) Filed: Dec. 7, 2010

(65) Prior Publication Data

US 2011/0152625 A1    Jun. 23, 2011

Related U.S. Application Data

(60) Provisional application No. 61/287,829, filed on Dec. 18, 2009.

(51) Int. Cl.
*A61B 1/32* (2006.01)

(52) U.S. Cl. ........................................................ 600/208

(58) Field of Classification Search ........... 600/201–246
See application file for complete search history.

(56) References Cited

U.S. PATENT DOCUMENTS

| | | | |
|---|---|---|---|
| 3,058,761 A * | 10/1962 | Christophersen | ............. 285/281 |
| 4,112,932 A | 9/1978 | Chiulli | |
| 4,334,688 A | 6/1982 | Spargo et al. | |
| 4,553,760 A | 11/1985 | Reed et al. | |
| 4,641,842 A | 2/1987 | Kataoka | |
| 4,723,550 A | 2/1988 | Bales et al. | |
| 4,844,483 A | 7/1989 | Iijima et al. | |
| 5,634,908 A | 6/1997 | Loomas | |
| 5,720,759 A | 2/1998 | Green et al. | |
| 5,807,237 A | 9/1998 | Tindel | |
| RE36,702 E | 5/2000 | Green et al. | |
| 6,942,671 B1 | 9/2005 | Smith | |
| 7,632,250 B2 | 12/2009 | Smith et al. | |
| 7,842,013 B2 * | 11/2010 | Haberland et al. | ........ 604/167.03 |
| 7,951,118 B2 * | 5/2011 | Smith et al. | ............... 604/167.01 |
| 8,162,894 B2 * | 4/2012 | Valaie | ...................... 604/167.01 |
| 2006/0189920 A1 | 8/2006 | Seeh | |
| 2008/0125716 A1 | 5/2008 | Cruz | |

OTHER PUBLICATIONS

European Search Report dated May 20, 2011 for the corresponding application EP 10252142, date of completion May 12, 2011.

* cited by examiner

*Primary Examiner* — Ellen C Hammond

(57) ABSTRACT

A surgical portal apparatus includes a portal housing, a portal sleeve, and a seal. The portal housing defines a central housing axis and a central housing channel. The portal sleeve extends from the portal housing and is dimensioned to pass through tissue to provide access to underlying tissue via a longitudinal opening. The central housing channel of the portal housing and the longitudinal opening of the portal sleeve define a passageway for reception and passage of a surgical object. The seal has inner surfaces defining a seal passage for establishing a general sealed relation about the surgical object. The seal passage is radially offset with respect to the central housing axis. The seal is adapted to rotate about the central housing axis to vary positioning of the seal passage to substantially maintain the substantial sealed relation upon manipulation of the surgical object within the portal housing.

13 Claims, 14 Drawing Sheets

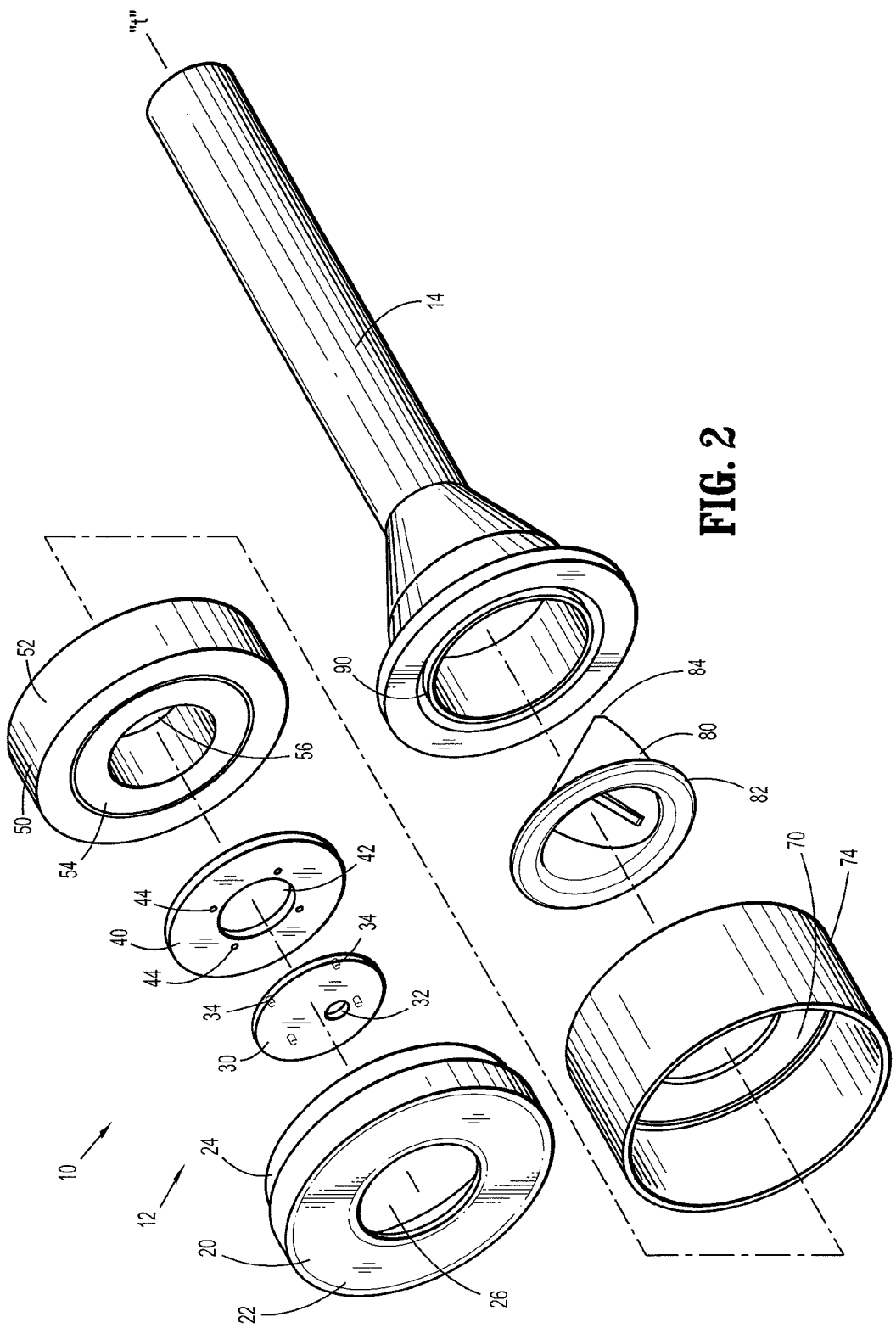

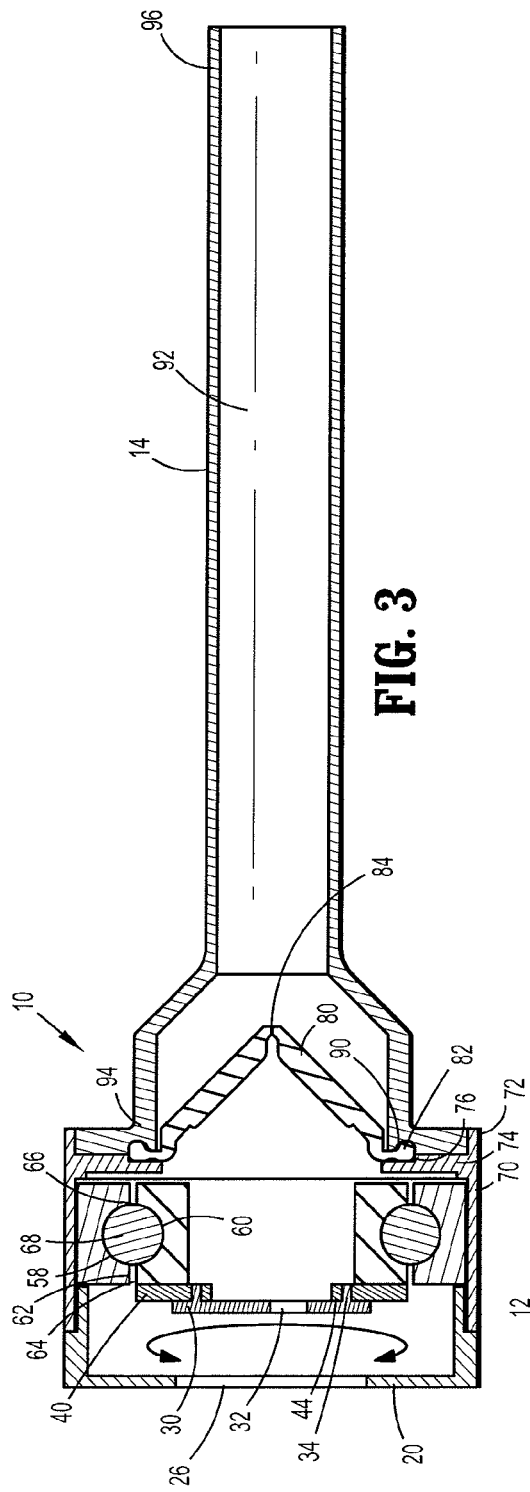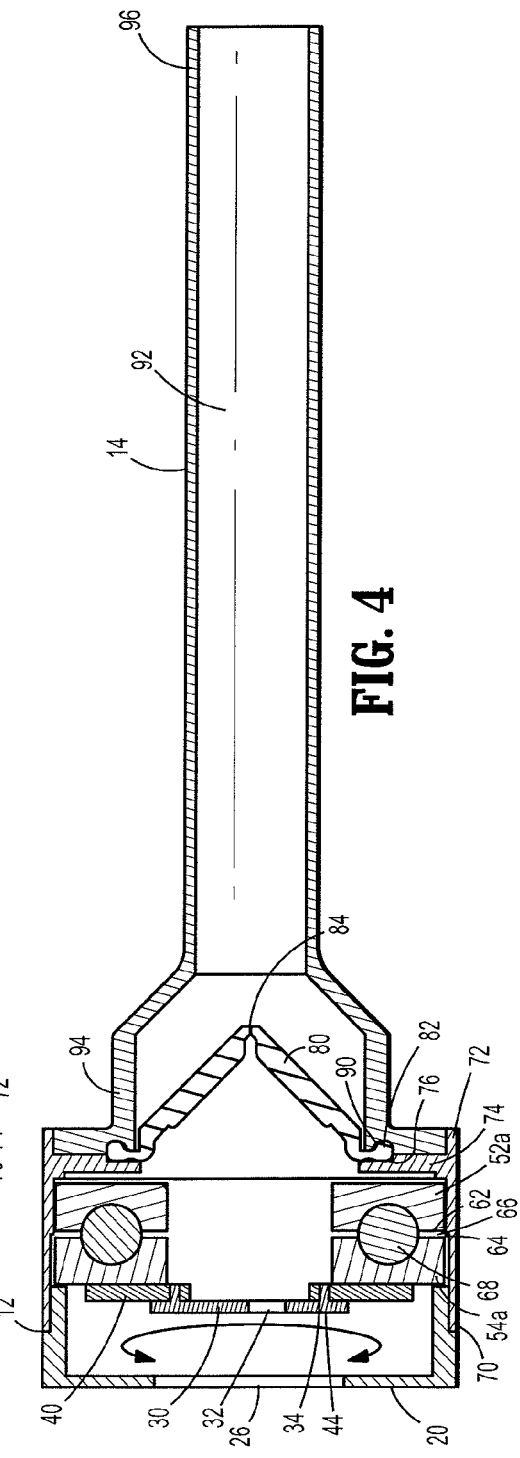

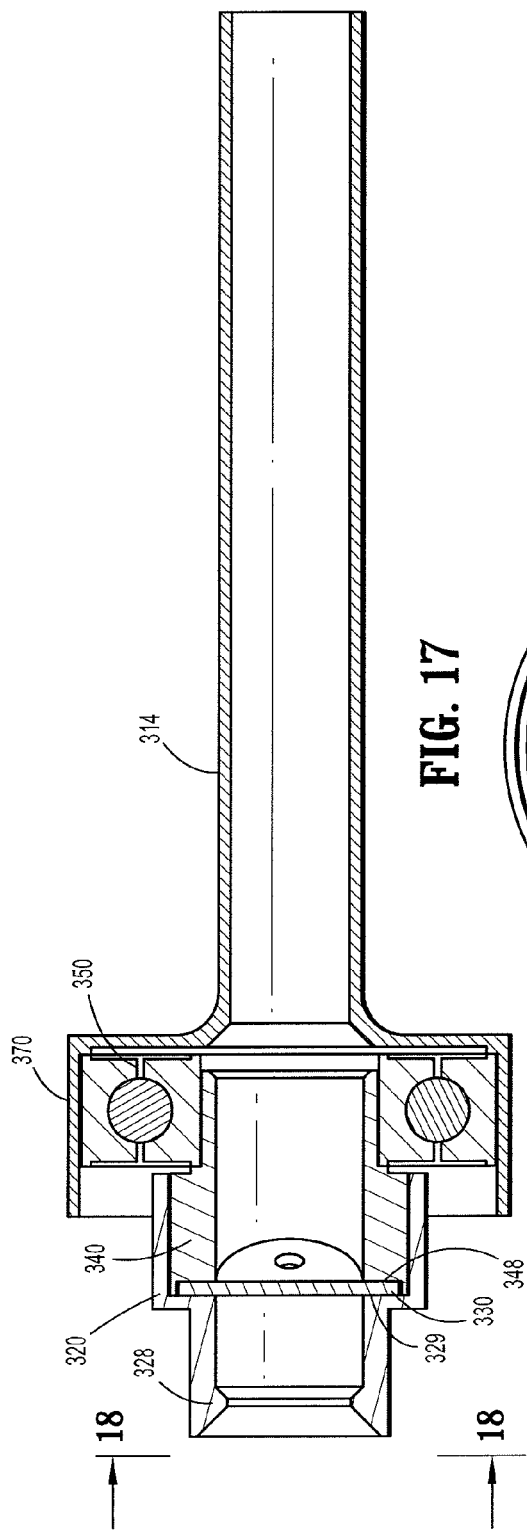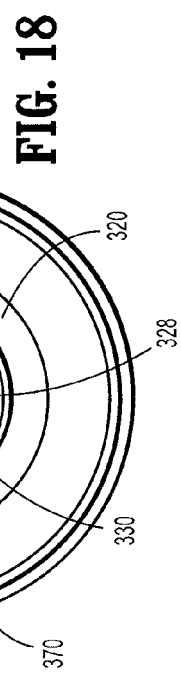
FIG. 17
FIG. 18

US 8,409,086 B2

SURGICAL PORTAL WITH ROTATING SEAL

CROSS REFERENCE TO RELATED APPLICATION

The present application claims the benefit of and priority to U.S. Provisional Application Ser. No. 61/287,829 filed on Dec. 18, 2009, the entire contents of which are incorporated herein by reference.

BACKGROUND

1. Field of the Disclosure

The present disclosure relates to surgical devices and, more particularly, relates to a surgical portal apparatus incorporating a rotating seal adapted for use during a minimally invasive surgical procedure.

2. Description of the Related Art

Minimally invasive surgical procedures, including endoscopic, arthroscopic, and laparoscopic procedures, permit surgery to be performed on organs, tissues, and vessels far removed from an opening within the tissue. These procedures generally require that any instrumentation inserted into the body be sealed, e.g., provisions may be made to ensure that gases do not enter or exit the body through the incision as, for example, in surgical procedures utilizing insufflating or irrigating fluids. These procedures typically employ surgical instruments which are introduced into the body through a cannula. The cannula has a seal assembly associated therewith. The seal assembly is intended to form a substantially fluid tight seal about the instrument to preserve the integrity of the established surgical site.

Seals may be limited by their ability to sustain a seal when it is moved off-axis relative to a central axis of a cannula. Seals may also be limited by their ability to sustain their integrity when an inserted surgical instrument is angulated. Such motions can create a "cat eye" or crescent shaped gap in the seal that can result in a loss of seal integrity. Additional problems include the flexibility of the seal in maintaining its integrity when both small diameter and large diameter surgical instruments are used.

SUMMARY

Accordingly, a surgical portal apparatus includes a portal housing, a portal sleeve, and a seal. The portal housing defines a central housing axis and a central housing channel. The portal sleeve extends from the portal housing and is dimensioned to pass through tissue to provide access to underlying tissue via a longitudinal opening. The central housing channel of the portal housing and the longitudinal opening of the portal sleeve define a passageway for reception and passage of a surgical object. The seal has inner surfaces defining a seal passage for establishing a general sealed relation about the surgical object. The seal passage is radially offset with respect to the central housing axis. The seal is adapted to rotate about the central housing axis to vary positioning of the seal passage to substantially maintain the substantial sealed relation upon manipulation of the surgical object within the portal housing.

A ball bearing assembly is mounted within the portal housing and is operably coupled to the seal to permit rotational movement of the seal about the seal axis. The ball bearing assembly includes a fixed ring, a rotating ring, and at least two ball bearings disposed within a track formed by the rings. The rotating ring is in communication with the seal so that the seal passage of the seal rotates about the central housing axis. In embodiments, the fixed ring of the ball bearing assembly is an outer ring affixed to the portal housing and the rotating ring is an inner ring that freely rotates radially with the ball bearings. In other embodiments, the fixed ring is a distal ring affixed to the portal housing and the rotating ring is a proximal ring that freely rotates radially over the ball bearings.

The portal apparatus may include a manually engageable actuator operatively coupled to the seal and extending from the portal housing. The actuator is movable to cause corresponding rotational movement of the seal about the central housing axis.

In embodiments the seal is substantially planar and defines an aperture, the aperture being the seal passage. The seal may be substantially orthogonal to the central housing axis or may be substantially obliquely arranged with respect to the central housing axis. In other embodiments, the seal defines a general funneled profile, such as an oblique circular cone, having an aperture, the aperture being the seal passage.

BRIEF DESCRIPTION OF THE DRAWINGS

Embodiments of the present disclosure will be better appreciated by reference to the drawings wherein:

FIG. 2 is a perspective view, with parts separated, of the seal assembly and the sleeve of FIG. 1;

FIG. 3 is a side cross-sectional view of the portal apparatus of FIGS. 1 and 2;

FIG. 4 is a side cross-sectional view of the portal apparatus of FIG. 1 with an alternative ball bearing assembly arrangement;

FIG. 17 is a side cross-sectional view of the portal apparatus of FIG. 14 taken along line 17-17 of FIG. 16;

FIG. 18 is a top view of the portal apparatus of FIG. 14 taken along line 18-18 of FIG. 17.

DETAILED DESCRIPTION

Figure 1:
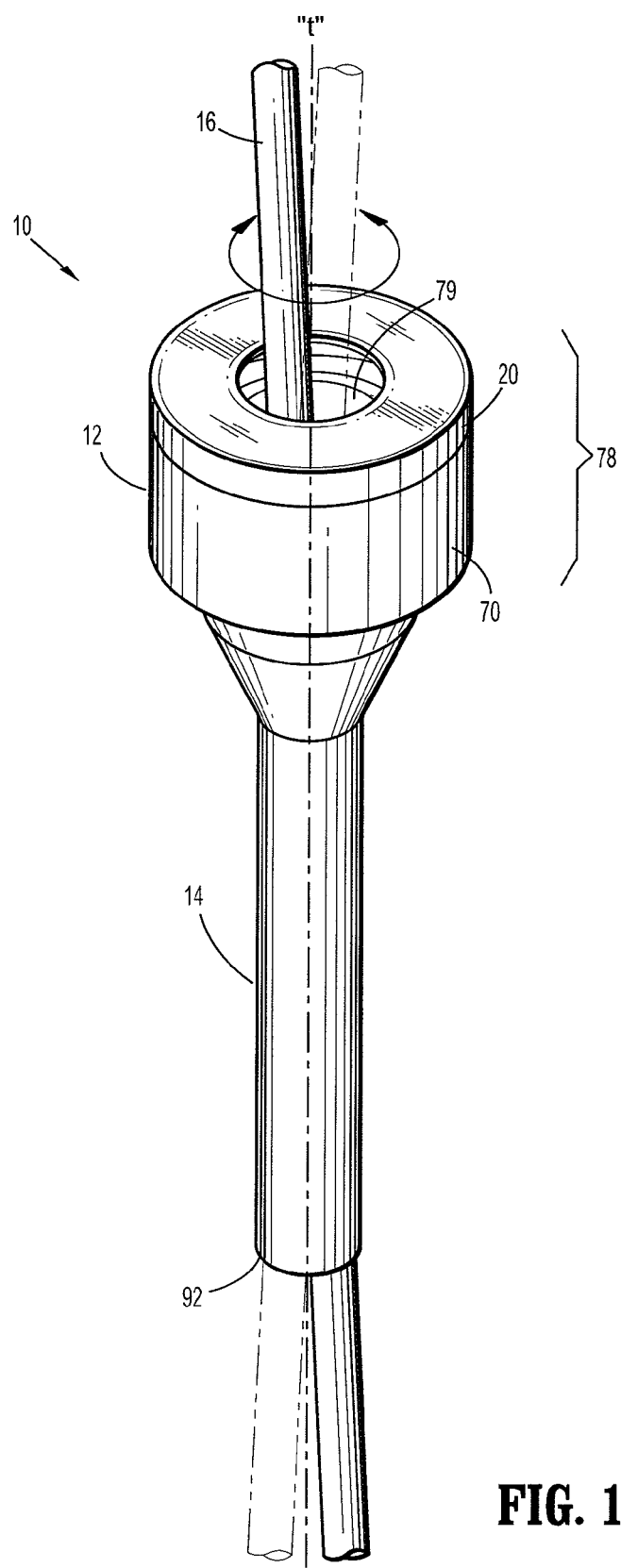
FIG. 1 is a perspective view of a portal apparatus in the form of a seal assembly and a sleeve in accordance with the principles of the present disclosure.

The portal apparatus of the present disclosure incorporates a seal assembly either alone or in combination with a sleeve for introduction into a body cavity of a patient. The portal apparatus is adapted for receiving objects therethrough. The seal assembly incorporates a seal which, either alone or in combination with a valve, provides a substantial seal between a body cavity of a patient and the outside atmosphere before, during, and after insertion of an object through the portal assembly. The seal assembly includes a ball bearing assembly for rotating the seal, and thus objects inserted therethrough, to different positions without compromising the integrity of the seal.

The seal assembly contemplates the introduction and manipulation of various types of instrumentation adapted for insertion through a trocar, cannula, or other portal assembly. A fluid tight interface is maintained via the seal about the inserted instrumentation. This substantially prevents gas and/or liquid leakage from the established surgical site so as to preserve the atmospheric integrity of a surgical procedure.

The seal is capable of accommodating objects of varying diameters, e.g., instruments from about 3 mm to about 18 mm, by providing a fluid tight seal with each object when inserted. The flexibility of the seal greatly facilitates endoscopic surgery where a variety of instruments having differing diameters are often needed during a single surgical procedure. Examples of surgical instrumentation which may be introduced through the portal apparatus include clip appliers, graspers, dissectors, retractors, staplers, laser probes, photographic devices, endoscopes, laparoscopes, arthroscopes, tubes, electrosurgical cutting, coagulating, and ablation devices, and other tools within the purview of those skilled in the art. Such instruments will be collectively referred to herein as "instruments" or "instrumentation."

Embodiments of the presently disclosed surgical portal apparatus will now be described in detail with reference to the drawing figures wherein like reference numerals identify similar or identical elements. As used herein and as is traditional, the term "distal" refers to that portion which is furthest from the user while the term "proximal" refers to that portion which is closest to the user.

Referring now to the drawings, FIG. 1 illustrates a portal apparatus 10 of the present disclosure incorporating seal assembly 12 mounted to portal sleeve 14. In embodiments, the portal apparatus 10 is particularly adapted for use in laparoscopic surgery where the peritoneal cavity is insufflated with a suitable gas, e.g., $CO_2$, to raise the cavity wall from the internal organs therein. The sleeve 14 is typically used with an obturator assembly (not shown) which may be a blunt, non-bladed, or sharp pointed instrument positionable within the passageway of the sleeve 14. The obturator assembly is utilized to penetrate a body wall or introduce the sleeve 14 through the body wall, and then subsequently is removed from the sleeve 14 to permit introduction of surgical instrumentation 16 utilized to perform the procedure through the passageway and body wall. Instrument 16 is shown rotating in phantom within seal assembly 12 and sleeve 14.

Seal housing 70 and end cap 20 define a portal housing 78 for housing the components of the seal assembly 12 as will be discussed. Portal housing 78 define a central housing axis "t" extending along the length of the seal assembly 12 and mounted sleeve 14 such that a central housing channel 79 of the portal housing 78 is in general alignment with passageway 92 of sleeve 14 for passage of surgical instruments 16 to underlying tissue.

With reference now to FIGS. 2-3, in conjunction with FIG. 1, an embodiment of a portal apparatus 10 of the present disclosure will be discussed. Portal apparatus 10 includes seal assembly 12 which includes end cap 20, instrument seal 30, attachment plate 40, ball bearing assembly 50, and seal housing 70. Sleeve 14 is detachably mountable to seal housing 70 of seal assembly 12 and duck bill valve 80 may optionally be configured to be in mechanical cooperation with both the seal assembly 12 and the sleeve 14.

End cap 20 is generally tubular in shape and includes a proximal end portion 22 and a distal end portion 24. An opening 26 is defined within proximal end portion 22 and is aligned with central housing axis "t" for receiving a surgical instrument. Opening 26 has a sufficient diameter to permit passage of relatively large sized instruments into central housing channel 79. End cap 20 may be removably coupled with seal housing 70 of seal assembly 12.

Instrument seal 30 is disposed distal to end cap 20 and may be any conventional type of seal as within the purview of those skilled in the art. Instrument seal 30 may be formed from a single material or combinations thereof. Instrument seal 30 may be fabricated from a suitable biocompatible relatively rigid material such as polypropylene, nylon, ABS, polycarbonate, stainless steel, titanium or any other suitable material. Instrument seal 30 may also be composed of fabric, elastomers, foam, combinations thereof, or combinations with other materials.

Instrument seal 30 is generally disc-shaped and defines an aperture, slit, or other seal passage 32 for reception and passage of surgical object or instrument 16. Seal passage 32 is configured to form a fluid-tight fit with surgical instrument 16. Seal passage 32 is off-set from the longitudinal mid-point of axis "t" such that it is off-axis and may rotate radially around central housing axis "t" while maintaining a substantially sealed relation with an inserted surgical instrument as will be discussed.

Instrument seal 30 is releasably couplable to a proximal surface of attachment plate 40 via joining members 34. The joining members 34 may be mechanically couplable to complementary joining members 44 on attachment plate 40 as illustrated in the current embodiment by way a pin 34 and slot 44 arrangement. Instrument seal 30 may be releasably secured or connected to attachment plate 40 by other conventional mechanical means including, for example, other male/female fasteners, bayonet couplings, threaded connections, snap fit, friction fit, tongue and groove arrangements, and cam-lock mechanisms. Instrument seal 30 may be chemically couplable to attachment plate 40 via use of adhesives or permanently couplable via ultrasonic welding or the like. Alternatively, instrument seal 30 may have no mating members but be frictionally engaged with attachment plate 40.

Attachment plate 40 is an annular plate including central opening 42 which is substantially aligned with opening 26 of end cap 20 and has a diameter of a sufficient size to accommodate the off-set and rotatable seal passage 32 of the instrument seal 30 in order to maintain the passageway for a surgical instrument. Attachment plate 40 includes mating features on both proximal and distal surfaces. Joining members 44 to instrument seal 30 are disposed on the proximal surface and means for coupling to ball bearing assembly 50 are disposed on the distal surface. Attachment plate 40 may be coupled to ball bearing assembly 50 by any of the means, such as those discussed above with respect to instrument seal 30.

Ball bearing assembly 50 includes two concentric rings including fixed ring 52 and rotating ring 54 defining opening 56 along longitudinal axis "t." Fixed ring 52 and rotating ring 54 each include a recess 58, 60 respectively, defined in facing walls 62, 64 to form track 66 for ball bearings 68. In the current embodiment, fixed ring 52 is an outer ring in communication with and attached to the seal housing 70 and rotating ring 54 is an inner ring operably connected to attachment plate 40 and thus seal 30 for free rotation of the seal 30. Other orientations are envisioned, such as shown in FIG. 4. FIG. 4 illustrates a stacked configuration where fixed ring 52a is distal to rotating ring 54a. Fixed ring 52a is attached to seal housing 70 and rotating ring 154 is free to rotate.

At least two ball bearings 68 are disposed between fixed and rotating rings 52, 54. Ball bearings 68 may be freely disposed within track 66 to travel around track 66 and radially rotate about the longitudinal axis "t," as well as spin about themselves. Ball bearings 68 may be held constant by a ball bearing holder (not shown) within track 66 so that the ball bearings 68 may only spin, for example, in an internal ring such as in thrust, rolling, or ball and groove bearing assembly. Alternatively, fixed ring 52 may include the ball bearing holders so that an area of the ball bearings 68 is exposed for contact with rotating ring 54.

Ball bearings 68 may be formed from metals, such as stainless steel, iron, and aluminum, as well as polymers, ceramics, and other rigid materials capable of supporting the rotating ring and permitting free rotation thereof with minimum friction. Ball bearings 68 may be spherical, ovoid, or other shapes which reduces the rotational friction of the rotating ring. In embodiments, a lubricant, such as grease, may be utilized to assist with smooth rotational movement of seal 30.

Seal housing 70 houses the components of the seal assembly 12 and also includes sleeve mounting collar 72 for joining the seal assembly 12 with sleeve 14. An annular septum 74 separates the sleeve mounting collar 72 from the rest of the components of the seal assembly 12. Sleeve mounting collar 72 may be selectively releasably connectable to sleeve 14 to cooperatively releasably couple seal assembly 12 to sleeve 14. Various means for releasably securing or connecting sleeve mounting collar 72 to proximal end 94 of sleeve 14 are envisioned including a bayonet coupling, snap-fit, frictional fit, tongue and groove arrangement, threaded arrangement, cam-lock mechanisms or the like. As illustrated in the current embodiment, sleeve mounting collar 72 is secured to sleeve 14 via friction fit. Seal assembly 12 may be mounted to sleeve 14 before, during, or after, application of sleeve 14 within the operative site. Alternatively, seal assembly 12 may be permanently secured to sleeve 14 by conventions means, such as for example, ultrasonic welding, use of adhesives, or by monolithically forming seal housing 70 with sleeve 14.

Optionally, a valve 80 may be disposed between seal housing 12 and sleeve 14. Annular septum 74 of seal housing 70 may include a notch 76 for securing valve 80 and sleeve 14 may include a channel 90 in proximal end 94 in which lip 82 of valve 80 may be seated. Valve 80 may be a zero-closure valve such as a duck-bill valve having a slit 84 which is adapted to close in the absence of a surgical object and/or in response to insufflation gases of the pressurized cavity. In the alternative, valve 80 may be a gel seal, balloon valve, or a flapper valve. Valve 80 may be fabricated from a relatively rigid material such as medical grade stainless steel or a biocompatible polymeric material. Valve 80 may also be formed from a flexible material such as a fabric, foam, or elastomeric material in order to bend or deform about an inserted instrument while absorbing off-axis motion. Further, valve 80 can minimize formation or gaps around an inserted instrument and prevents fluid or debris from entering seal assembly 12 when the valve 80 is closed. Fluid pressure on valve 80 will close slit 84 thereby sealing seal assembly 12 from fluids. When an instrument is inserted through valve 80, however, a seal is not always formed around the instrument thereby allowing some fluid to enter seal housing 70 wherein seal 30 prevents the fluid from exiting seal assembly 12.

Sleeve 14 may be any portal member suitable for the intended purpose of accessing a body cavity and typically defines a passageway 92 permitting introduction of instruments 16 therethrough. Sleeve 14 has proximal (or leading) and distal (or trailing) ends 94, 96. Sleeve 14 may be formed of any suitable medical grade material, such as metal materials like stainless steel, titanium, and aluminum; polymeric materials like acrylonitrile-butadiene-styrene, polycarbonate, and polystyrene; and other rigid materials and combinations thereof as envisioned by one skilled in the art.

Sleeve 14 may be transparent, translucent, or opaque. The diameter of sleeve 14 may vary, but, typically ranges from about 3 to about 18 mm. Sleeve 14 may or may not include means for facilitating retention of the sleeve 14 within tissue. Such means include a plurality of locking elements, ribs, or other locking arrangements within the purview of those skilled in the art.

The assembly of portal apparatus 10 will now be discussed. Attachment plate 40 is secured to rotating ring 54 of ball bearing assembly 50 as well as seal 30. The joined components are advanced within seal housing 70. Fixed ring 52 may be affixed to seal housing 70 and end cap 20 may be secured thereon. Assembled seal assembly 12 may then be secured to sleeve 14 as discussed above, optionally valve 80 secured therebetween.

Figure 5:
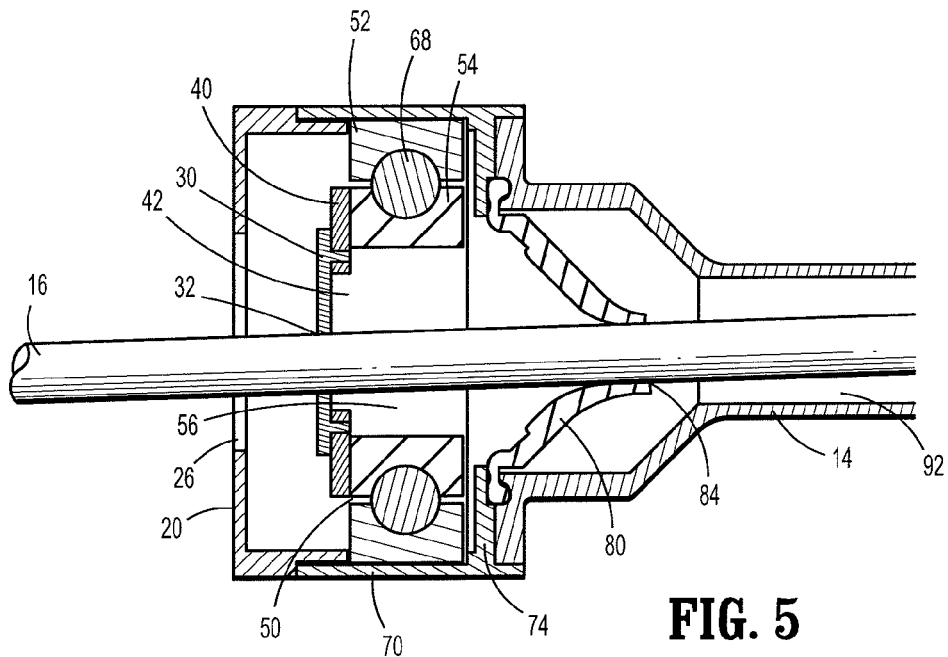
FIG. 5 is an enlarged cross-sectional view of the seal assembly depicted in FIG. 3 with an instrument inserted therethrough.
Figure 6:
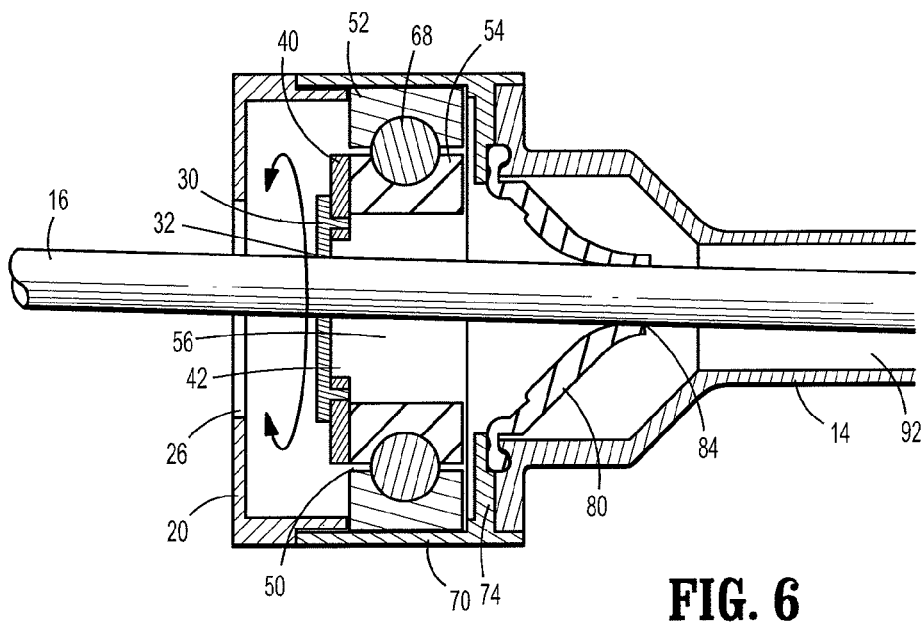
FIG. 6 is a side cross-sectional view of FIG. 5 with the instrument rotated therein.

In use, as illustrated in FIGS. 5 and 6, instrument 16 is advanced distally through opening 26 of end cap 20 through seal passage 32 of seal 30, opening 42 of attachment plate 40, opening 56 of ball bearing assembly 50, through annular septum 74 of seal housing 70, slit 84 of valve 80, and passageway 92 of sleeve 14. The desired surgical task is performed with instrument 16. Instrument 16 may be re-positioned during the surgical procedure by rotating the instrument 16 about the central housing axis "t" thereby rotating the rotating ring 54 which contacts and spins ball bearings 68. Free rotation of ball bearings 68 reduces rotational friction and allows smooth movement and rotation of seal 30 and thus instrument 16.

Figure 7:
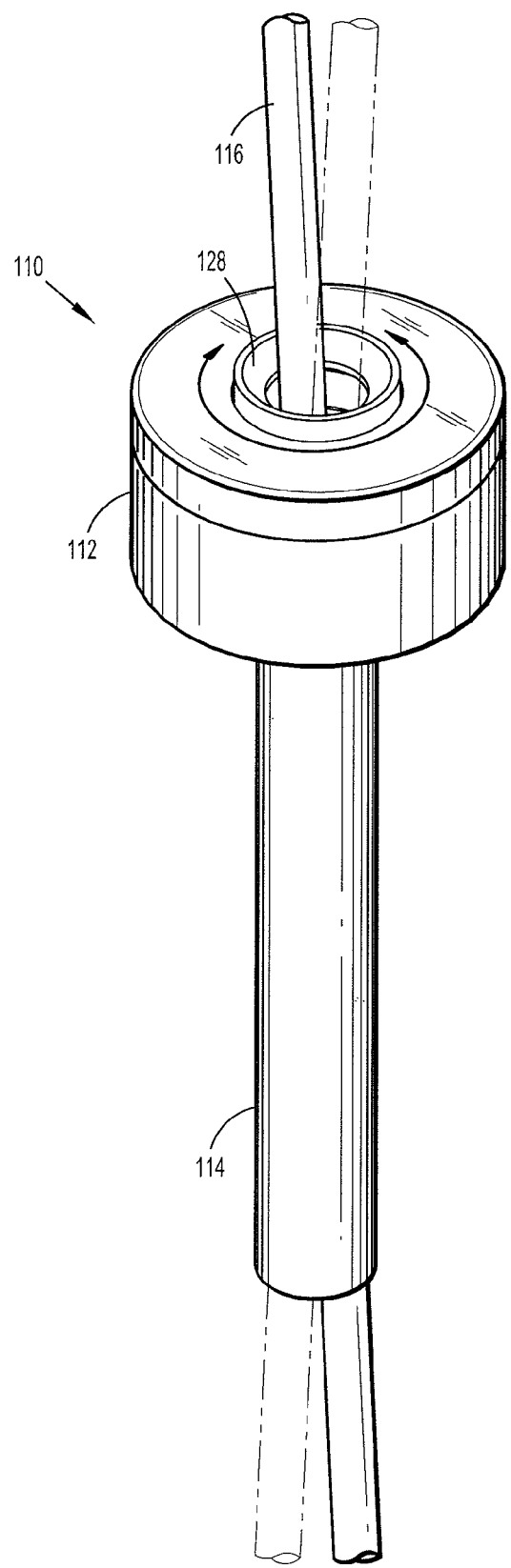
FIG. 7 is a perspective view of an alternate embodiment of a portal apparatus in accordance with the principles of the present disclosure.
Figure 8:
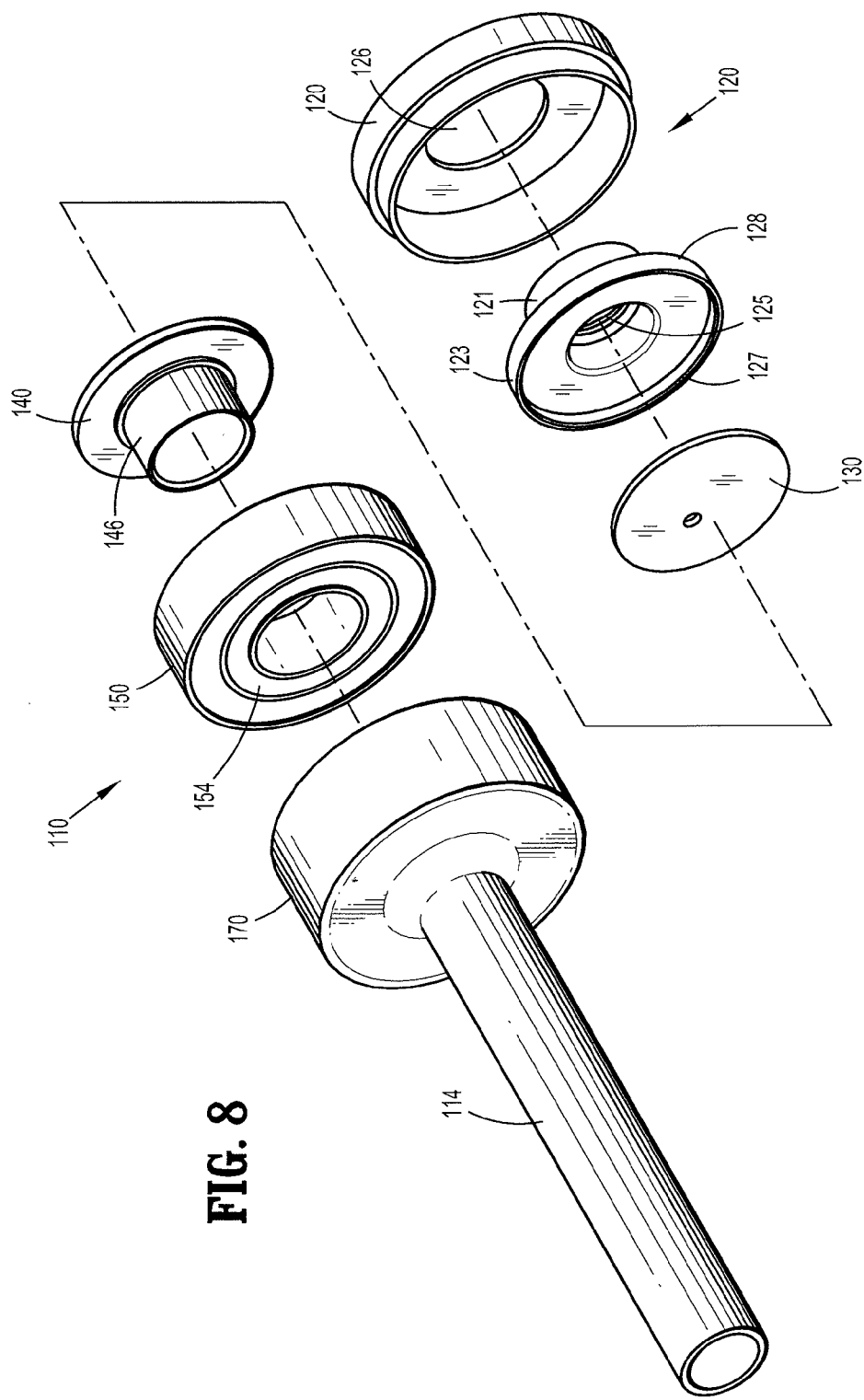
FIG. 8 is a perspective view, with parts separated, of the seal assembly and the sleeve of FIG. 7.
Figure 9:
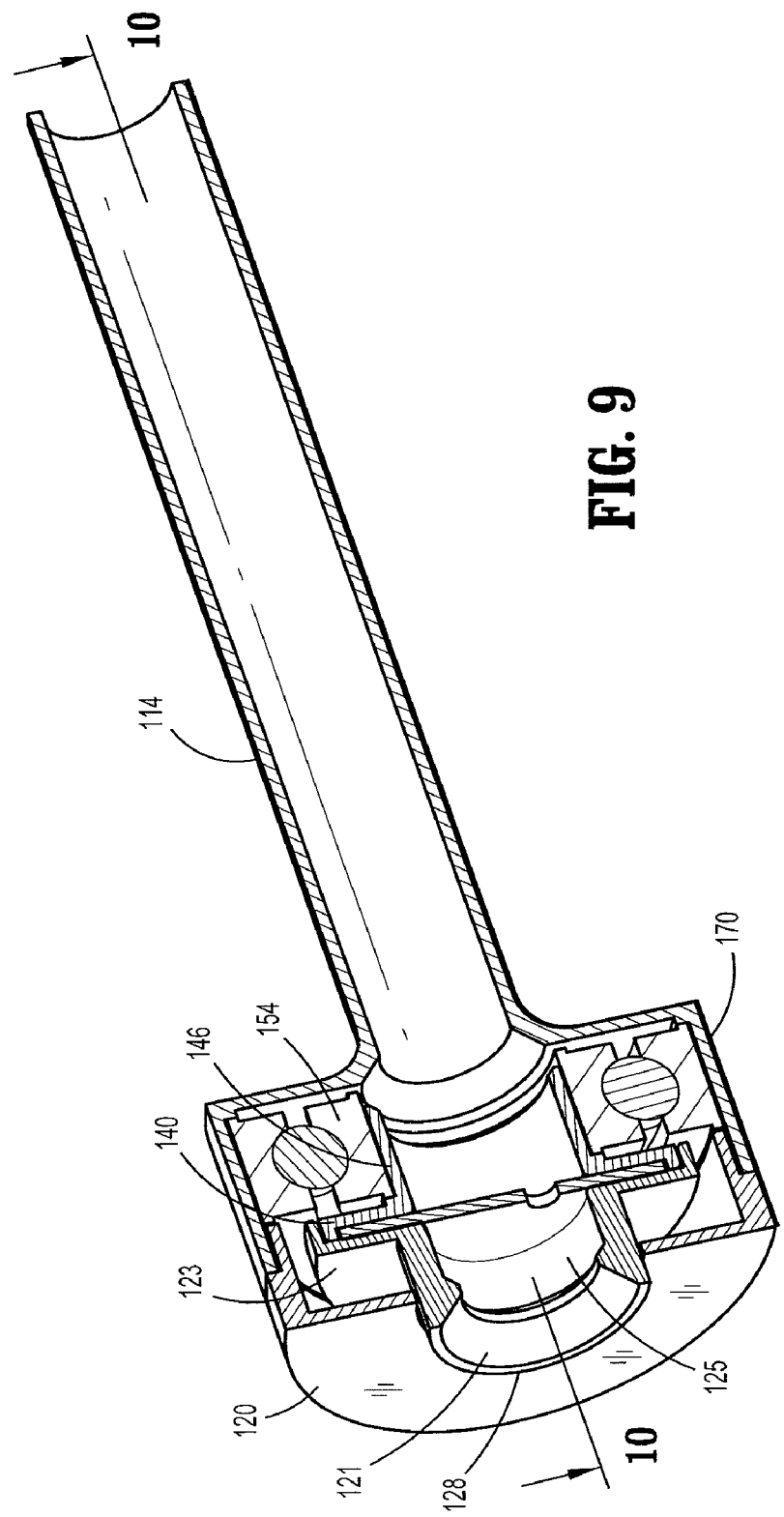
FIG. 9 is a perspective cross-sectional view of the portal apparatus of FIG. 7.
Figure 10:
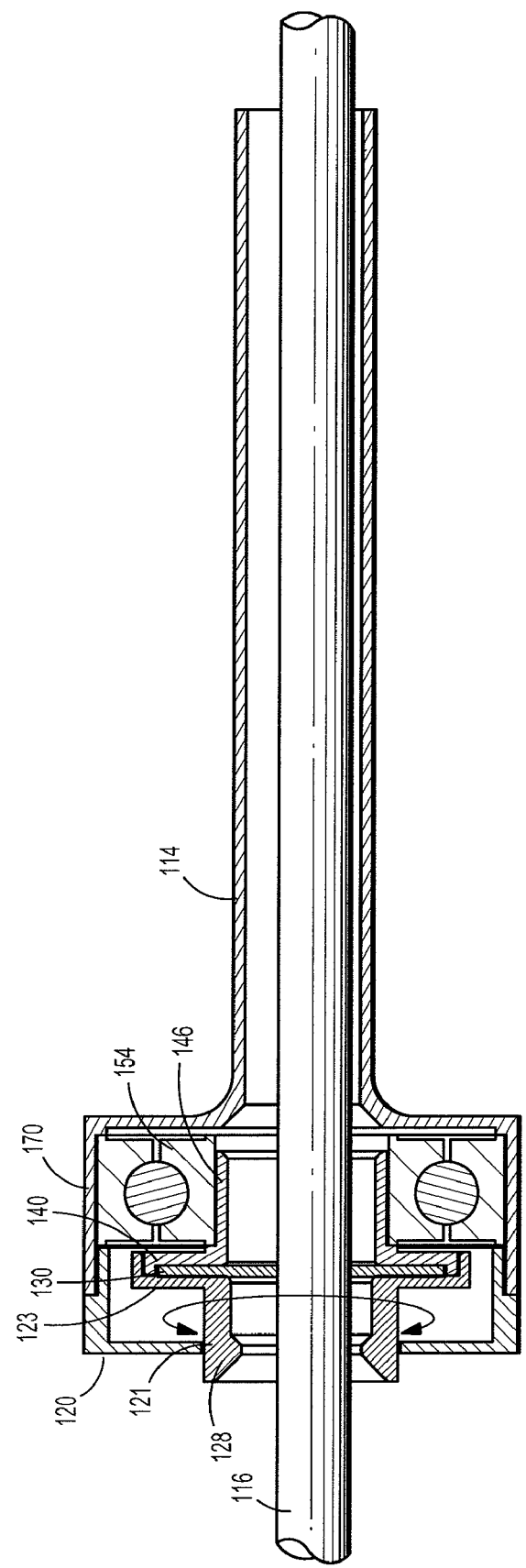
FIG. 10 is a side cross-sectional view of the portal apparatus of FIG. 7 taken along line 10-10 of FIG. 9 with an instrument inserted therethrough.

Alternatively, as depicted in FIG. 7, the portal apparatus may contain a feature that allows rotation of the instrument about axis "t" without having to manually turn the instrument itself. FIGS. 8-10, in conjunction with FIG. 7, illustrate another embodiment of the presently described portal apparatus 110. Portal apparatus 110 includes seal assembly 112 and portal sleeve 114. Like components are similarly numbered as those illustrated in FIGS. 1-6. Seal assembly 112 includes a manually engageable actuator 128 disposed between end cap 120 and seal 130. Actuator 128 may be any mechanical device, such as a knob, dial, or lever which a user may move to rotate surgical instrument 114. Actuator 128 includes an upper portion 121 for placement through opening 126 of end cap 120 such that it extends from portal housing 178 for gripping by the user and a lower portion 123 for contacting seal 130. Upper portion 121 includes a central aperture 125 for passing surgical instruments. Lower portion 123 may include a lip 127, or other joining means, for retaining seal 130. Accordingly, manual rotation of upper portion 121 of actuator 128 will cause corresponding rotational movement of seal 130 thereby rotating instrument 116 passed therethrough about axis "t."

Additionally, attachment plate 140 may include a lower collar 146 to aid in proper alignment of attachment plate 140 with rotating ring 154 of ball bearing assembly 150. Alternatively, lower collar 146 may also provide a friction fit with rotating ring 154 thereby obviating the need for a mechanical or chemical attachment as described above.

Figure 11:
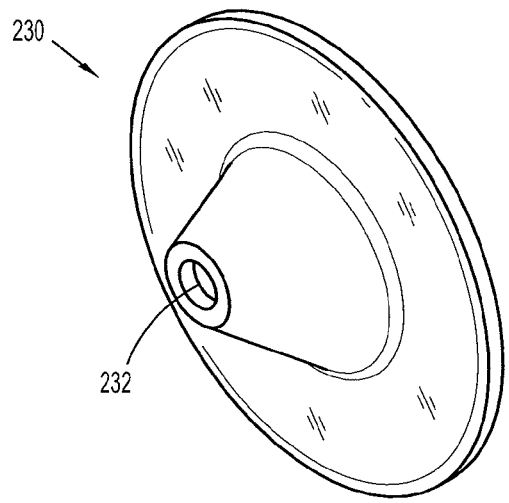
FIG. 11 is a perspective view of a seal in accordance with the present disclosure.
Figure 12:
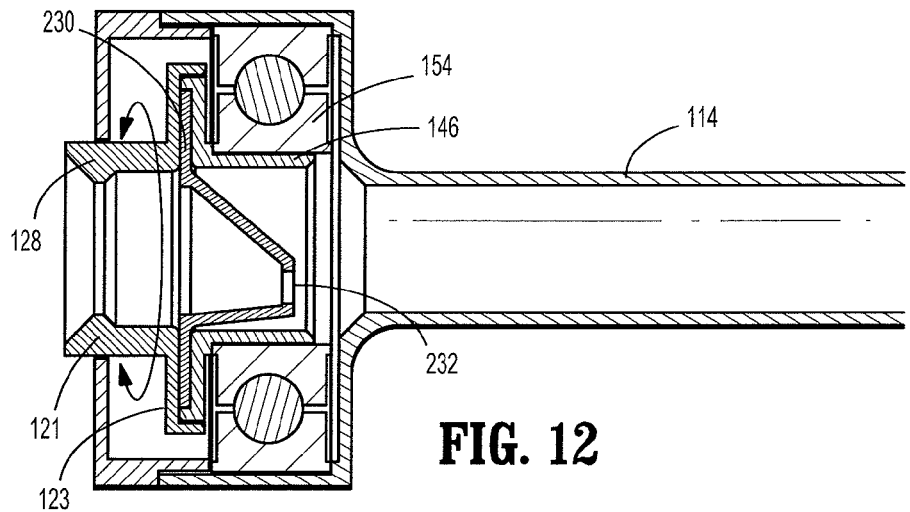
FIG. 12 is a side-cross-sectional view of the portal apparatus of FIG. 7 utilizing the seal of FIG. 11.
Figure 13:
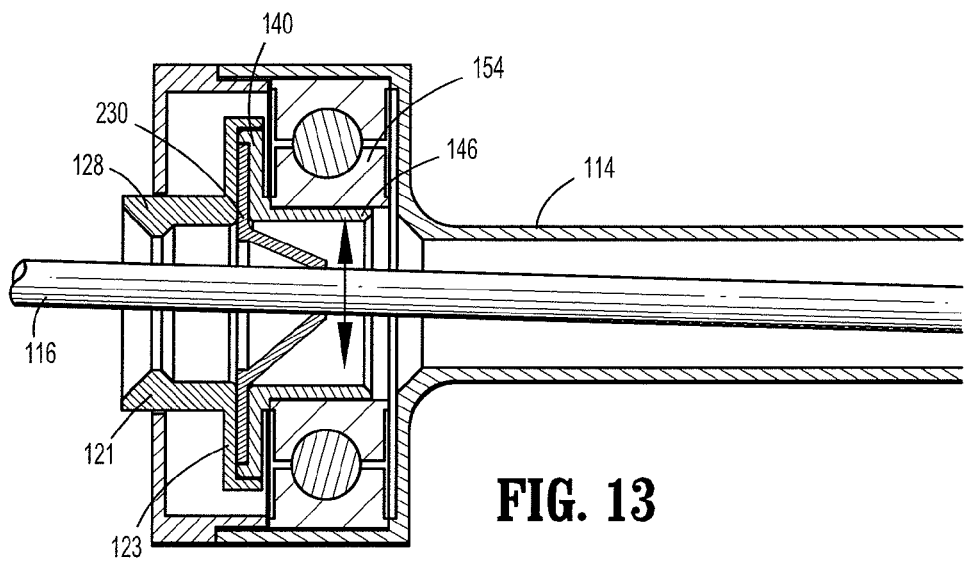
FIG. 13 is a side cross-sectional view of the portal apparatus of FIG. 12 having an instrument inserted therethrough.
Figure 14:
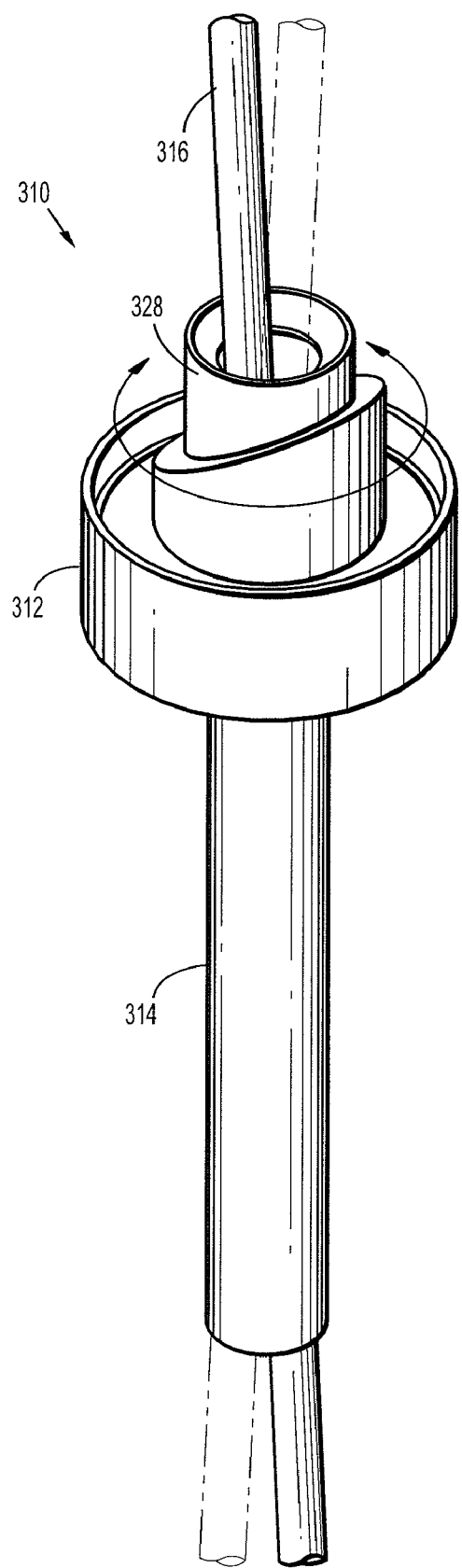
FIG. 14 is a perspective of an alternate embodiment of a portal apparatus in accordance with the principles of the present disclosure.
Figure 15:
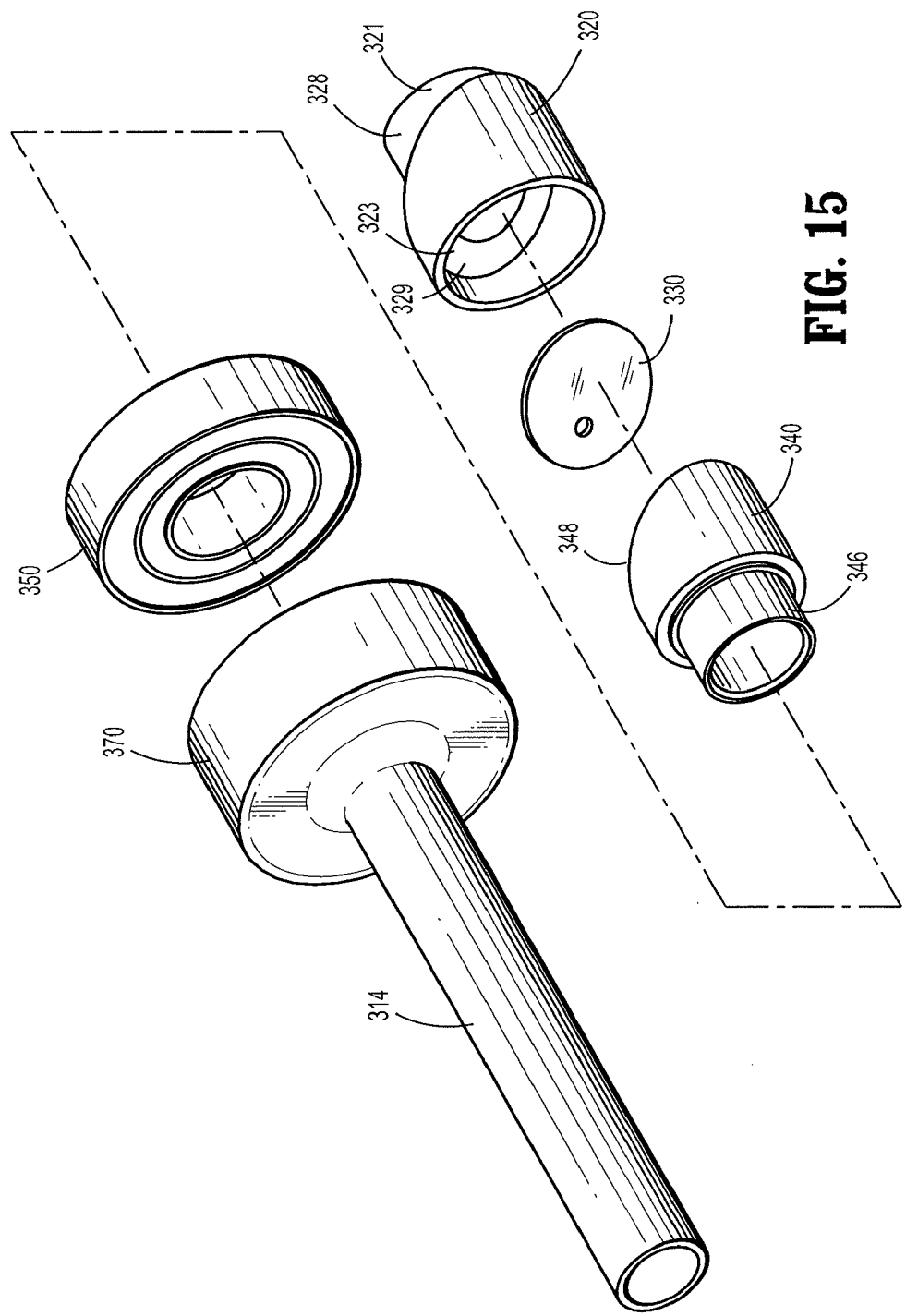
FIG. 15 is a perspective view, with parts separated, of the seal assembly and the sleeve of FIG. 14.
Figure 16:
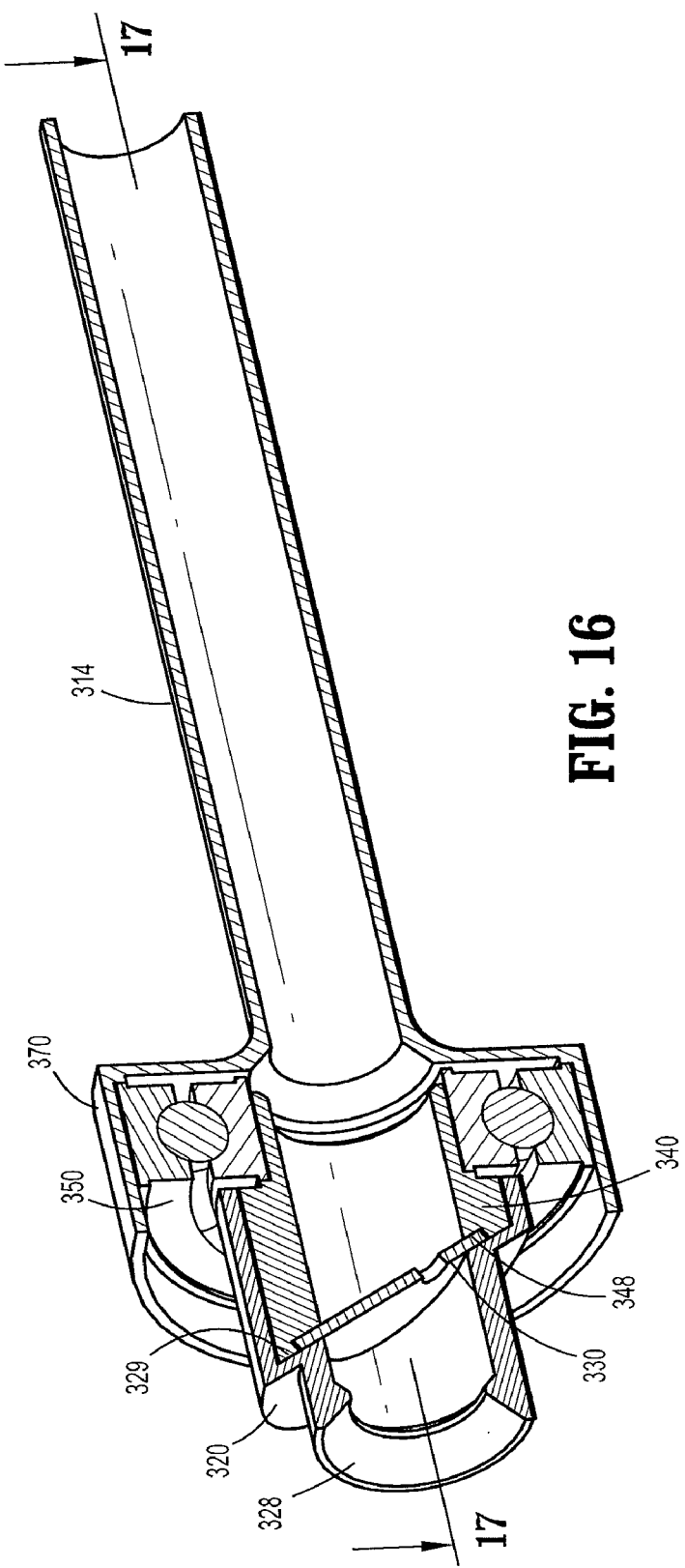
FIG. 16 is a perspective cross-sectional view of the portal apparatus of FIG. 14.
Figure 19:
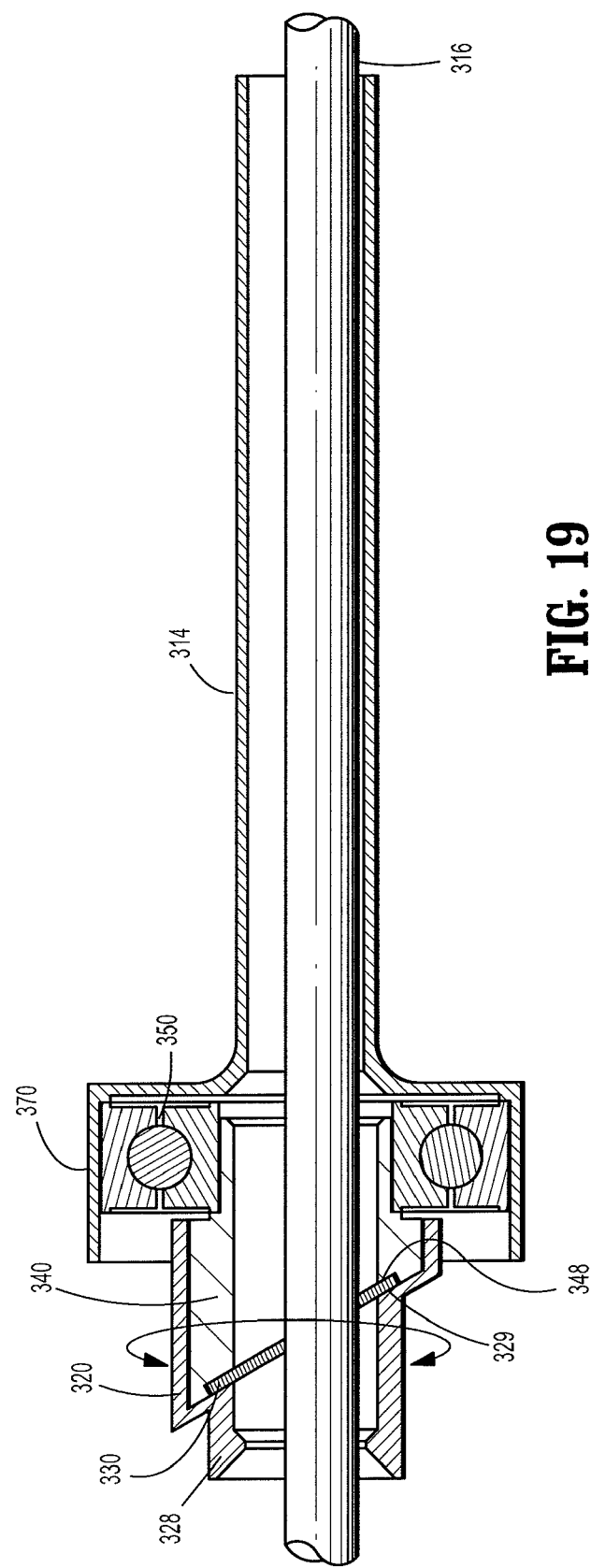
FIG. 19 is a side cross-sectional view of the portal apparatus of FIG. 14 with an instrument inserted therethrough.

As illustrated in the current embodiments, seal 130 is flat or planar. It is envisioned that the seal may define different shapes having an off-set opening, such as that shown in FIG. 11, for sealing and maintaining the integrity of the established surgical site. FIGS. 11-13 illustrates seal 230 defining a generally tapered or funneled conical profile in the form of an oblique circular cone whereby the inner area of the seal 230 slopes at an oblique angle with respect to the central housing axis "t" to define aperture 232 which is off-axis from axis "t." The funneled characteristic may assist in guiding the instrument toward aperture 232 during initial introduction of the instrument or object and may substantially minimize the potential of inversion of seal 230 during withdrawal of the instrument. The conical seal may also flex in addition to rotate thereby allowing some additional off-axis motion as illustrated by the arrows in FIG. 13.

Seal 130 of FIGS. 7-10 is also illustrated as being substantially orthogonal to the central housing axis "t." In embodiments, however, the seal may be angulated and substantially obliquely arranged with respect to the central housing axis "t." FIGS. 14-19 illustrate another embodiment of the presently described portal apparatus 310. Portal apparatus 310 includes seal assembly 312 and portal sleeve 314, with like components similarly numbered as the previous figures. Seal 330 may be positioned between and in contact with end cap 320 and attachment plate 340. Both the end cap 320 and the attachment plate 340 include an angulated surface 329, 348 respectively, between which seal 330 may be disposed at an oblique angle relative to the longitudinal axis "t."

To use seal assembly 112, 212, 312 and sleeve 114, 214 314 of the present disclosure in connection with the performance of a surgical task during a laparoscopic procedure, the peritoneal cavity is insufflated to establish the pneumoperitonum. Seal assembly 112 is mounted to sleeve 114 as discussed hereinabove. The assembled portal system 110 is introduced into an insufflated abdominal cavity typically utilizing a sharp or non-blade trocar obturator to access the cavity and the obturator is removed. An instrument 116 may be advanced through portal system 110 by inserting the instrument 116 into the seal assembly 112 via the openings defined by the actuator 128, end cap 120, seal 130, attachment plate 140, ball bearing assembly 150, and seal housing 170. The instrument 116 is then distally passed through sleeve 114 and into the body cavity. During performance of a surgical task, the instrument 116 may be manipulated and re-positioned by rotating either the instrument 116 or the actuator 128 about the longitudinal axis "t." Rotation of the instrument 116 or knob 128 rotates seal 130, attached attachment plate 140, and rotating ring 154 of ball bearing assembly 150. Radial movement of rotating ring 154 of the ball bearing assembly 150 spins ball bearings 168. Movement and rotation of the ball bearings 168 reduces the rotational friction on the rotating ring 154 and allows smooth movement and rotation of seal 130 and thus instrument 116.

It will be understood that various modifications and changes in form and detail may be made to the embodiments of the present disclosure without departing from the spirit and scope of the invention. Therefore, the above description should not be construed as limiting but merely as exemplifications of embodiments of the present disclosure. Those skilled in the art will envision other modifications within the scope and spirit of the present disclosure as defined by the claims appended hereto.

What is claimed is:

1. A surgical portal apparatus, which comprises:
   a portal housing defining a central housing axis and a central housing channel;
   a portal sleeve extending from the portal housing, the portal sleeve dimensioned to pass through tissue to provide access to underlying tissue and having a longitudinal opening, the central housing channel of the portal housing and the longitudinal opening of the portal sleeve defining a passageway for reception and passage of a surgical object;
   a seal having inner surfaces defining a seal passage for establishing a general sealed relation about the surgical object, the seal passage being radially offset with respect to the central housing axis, the seal being adapted to rotate about the central housing axis to vary positioning of the seal passage radially around the central housing axis to substantially maintain the substantial sealed relation upon manipulation of the surgical object within the portal housing; and
   a ball bearing assembly mounted within the portal housing and operatively coupled to the seal, the ball bearing assembly permitting rotational movement of the seal about a seal axis.

2. The surgical portal apparatus according to claim 1 wherein the ball bearing assembly includes a fixed ring, a rotating ring, and at least two ball bearings disposed within a track formed by the rings, the rotating ring in communication with the seal so that the seal passage of the seal rotates about the central housing axis.

3. The apparatus according to claim 2, wherein the fixed ring of the ball bearing assembly is an outer ring affixed to the portal housing and the rotating ring is an inner ring that freely rotates radially with the ball bearings.

4. The apparatus according to claim 2, wherein the fixed ring is a distal ring affixed to the portal housing and the rotating ring is a proximal ring that freely rotates radially over the ball bearings.

5. The apparatus according to claim 2, wherein the seal assembly further comprises an attachment plate for securing the seal to the rotating ring of the ball bearing assembly.

6. The apparatus according to claim 1, including a manually engageable actuator operatively coupled to the seal and extending from the portal housing, the actuator movable to cause corresponding rotational movement of the seal about the central housing axis.

7. The apparatus according to claim 1, wherein the seal is substantially planar and defines an aperture, the aperture being the seal passage.

8. The apparatus according to claim 7 wherein the seal is substantially orthogonal to the central housing axis.

9. The apparatus according to claim 7 wherein the seal is substantially obliquely arranged with respect to the central housing axis.

10. The apparatus according to claim 1, wherein the seal defines a general funneled profile.

11. The apparatus according to claim 10, wherein the seal defines an aperture, the aperture being the seal passage.

12. The apparatus according to claim 10, wherein the seal defines an oblique conical section.

13. The apparatus according to claim 1, including a zero-closure valve adapted to substantially close in the absence of the surgical object.

* * * * *